United States Patent [19]

Plummer et al.

[11] 4,423,234

[45] Dec. 27, 1983

[54] COPPER-CATALYZED BIAROMATIC COUPLING PROCESS

[75] Inventors: Ernest L. Plummer, North Tonawanda; David E. Seelye, Lockport, both of N.Y.

[73] Assignee: FMC Corporation, Philadelphia, Pa.

[21] Appl. No.: 378,539

[22] Filed: May 17, 1982

[51] Int. Cl.³ .............................................. C07C 2/00
[52] U.S. Cl. ...................................... 549/80; 546/346; 546/348; 548/560; 549/504; 549/506; 570/129; 570/182; 585/425
[58] Field of Search ................ 546/346, 348; 548/560; 549/80, 504, 506; 570/129, 182; 585/425

[56] References Cited

U.S. PATENT DOCUMENTS 4,214,004  7/1980  Plummer ............................ 424/305
4,329,518  5/1982  Plummer ............................ 568/807

OTHER PUBLICATIONS

Atkinson et al., *J. Am. Chem. Soc.,* 65, 476, (1943).
Cadogan, *J. Chem. Soc.,* 4257, (1962).
*Chem. Abstr.,* 54, 4489h, (1960).
Fanta, *Synthesis,* 9-21, (1974).

*Primary Examiner*—Richard Raymond
*Attorney, Agent, or Firm*—R. L. Hansen; H. R. Ertelt

[57] ABSTRACT

Improved yields of biaromatic compounds, e.g., unsymmetrical biphenyl compounds, result by incorporating metallic copper in a non-aqueous diazonium-type coupling reaction.

10 Claims, No Drawings

COPPER-CATALYZED BIAROMATIC COUPLING PROCESS

This invention is in the field of aromatic organic chemical synthesis, wherein a substituted aniline derivative is condensed with a second aromatic compound to produce an unsymmetrical biaromatic adduct. For example, this invention is an improved process for the production of unsymmetrical biphenyl compounds.

Substituted [1,1'-biphenyl]-3-ylmethyl compounds of the following structural formula, wherein Y is hydroxyl or a leaving group, A and B are substituent groups, a is 0–4, and b is 0–5, are intermediates in the preparation of pyrethroid insecticides.

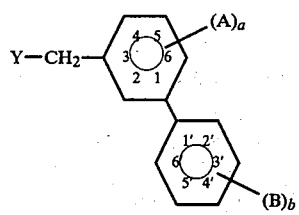

These intermediates and their utility are disclosed in U.S. Pat. No. 4,214,004, for example. A number of these compounds, including those of greatest commercial potential, are difficult to prepare, and low yields of these intermediates hamper development of pesticides incorporating them.

U.S. Pat. No. 4,329,518 discloses preparation of insecticide intermediate compounds of the aforesaid formula from 3-chloro-2-methyl[1,1'-biphenyl] and 2,3,4,6-tetrafluoro1,1'-biphenyl], together with their conversion to insecticides; that disclosure is incorporated by reference herein. According to the reference, these unsymmetrical biphenyl compounds were prepared in about 12% yield and 37% yield, respectively, by means of the diazonium coupling-type reaction described by Cadogan, *J. Chem. Soc.*, 4257 (1962).

It has now been found that yields in the process described by Cadogan can be increased substantially by incorporating metallic copper in the non-aqueous reaction mixture. The use of copper in the Ullmann coupling of aryl halides is well known, e.g., *Synthesis*, 9–21 (1974), and the use of copper in aqueous diazonium coupling reactions has been disclosed by Atkinson, et al., *J. Am. Chem. Soc.*, 65, 476 (1943).

Accordingly, in a process for preparing a biaromatic compound of the formula

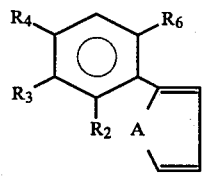

by treating an aniline derivative of the formula

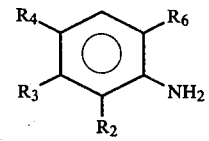

with a lower alkyl nitrite in a solvent of the formula

wherein $R_2$ is hydrogen, halogen, or lower alkyl, $R_3$ is hydrogen (unless $R_2$ is lower alkyl) or halogen, $R_4$ and $R_6$ are independently hydrogen or halogen, and A is —CH=CH—, —NH—, —CH=N—, oxygen, or sulfur, this invention is the improvement which comprises adding copper metal to the reaction mixture, thereby increasing the yield of the desired biaromatic compound.

For purposes herein, the term "lower alkyl" means a straight or branched chain of 1 to 6, preferably 1 to 4, carbon atoms. The terms "halo", "halogen", or "halide" mean fluorine, chlorine, and bromine.

The process of this invention is especially effective when A is —CH=CH— or S, and the product is an unsymmetrical biaromatic, especially biphenyl, compound. The invention is very useful in producing 3-chloro-2-methyl[1,1'-biphenyl] and 2,3,4,6-tetrafluoro[1,1'-biphenyl], as well as 3- or 4-chloro[1,1-'biphenyl].

In carrying out the process of this invention it is preferable to add the aniline derivative to a stirred, warm (30°–50° C.) mixture of the lower alkyl nitrite and powdered copper in the solvent. The solvent will be selected from benzene, pyrrole, pyridine, furan, and thiophene. The solvent should be in excess, at least about 50:1 on a molar basis with respect to the aniline derivative. When the addition is complete, it is usually desirable to heat the reaction mixture at about 60° C. to reflux for several hours.

Although lower alkyl nitrites in general are effective, t-butyl and i-amyl nitrites are readily available. The lower alkyl nitrite should be in excess, i.e., about 50% molar excess with respect to the aniline derivative.

The copper metal should be in powdered form. The amount is not critical, and 0.05 to 1.0 moles of copper per mole of aniline derivative is satisfactory.

Although not necessary to the reaction, the presence of a drying agent, such as molecular sieves, magnesium sulfate, or sodium sulfate, may sometimes be employed effectively. When used, approximately 50 grams of drying agent per mole of aniline derivative is employed.

The process of this invention will be more readily understood by reference to the following Examples in which temperatures are in degrees centigrade and pressures are in mm Hg.

EXAMPLE 1

Preparation of 3-Chloro-2-methyl[1,1'-biphenyl]

A stirred mixture of benzene (500 ml), t-butyl nitrite (15.5 g, 0.15 mole), copper powder (5.0 g) and 4Å molecular sieves (powdered, 5.0 g) was heated to 45°. A solution of 3-chloro-2-methylaniline (14.2 g, 0.1 mole)

in benzene (50 ml) was added dropwise to the mixture. The temperature of the reaction mixture rose to 56° during the addition. After complete addition, the reaction mixture was stirred at 52° for 16 hours, then at 60° for 24 hours. The excess benzene was then removed by distillation and the residue subjected to column chromatography on silica gel, elution with n-heptane. The solvent was removed by distillation to leave a red oil (8.77 g). The oil was distilled under reduced pressure to yield 3-chloro-2-methyl-[1,1'-biphenyl] (7.94 g, bp 84°/0.15 mm) as an oil. This experiment is designated Run 1/1 in the following tabulation of a number of experiments conducted with and without copper, but under otherwise similar conditions.

| Run | (Benzene)/(Aniline) | Temp | Yield |
| --- | --- | --- | --- |
| 1/1 | 62 moles/mole | 60° | 39% |
| 1/2 | 84 | 60 | 37 |
| 1/3 | 62 | 45 | 33 |
| 1/4 | 62 moles/mole | 45° | 38% |
| 1/5 | 62 | 45 | 38 |
| 1/6* | 56 | 45 | 30 |
| 1/7* | 112 | 45 | 35 |
| 1/8* | 56 | 45 | 25 |
| 1/9* | 62 | 45 | 23 |
| 1/10* | 11 | 80 | 15 |
| 1/11* | 23 | 45 | 14 |
| 1/12* | 11 | 80 | 10 |
| 1/13* | 20 | 80 | 14 |

*Run without copper; outside the scope of this invention.

On average, the yield was 21% in the absence of copper, but 37% when copper was employed according to this invention.

EXAMPLE 2

Preparation of 2,3,4,6-Tetrafluoro[1,1'-biphenyl]

During a 25 minute period, t-butyl nitrite (23.4 g, 0.23 mole) was added dropwise to a stirred mixture of 2,3,4,6-tetrafluoroaniline (25.0 g, 0.15 mole) and copper powder (9.6 g, 0.15 mole) in benzene (744 ml) at 50°, i.e., (benzene)/(aniline)=55 moles/mole. After complete addition, the mixture was heated at 70° for 30 minutes, then allowed to cool to room temperature. The reaction mixture was subjected to column chromatography on silica gel, elution with n-heptane. The solvent was removed under reduced pressure to leave a red oil (26.2 g) which solidified on standing. The solid was recrystallized from n-heptane:methylcyclohexane (3:2) to yield a light brown solid (7.1 g). The mother liquor was evaporated and the residue sublimed under reduced pressure to yield a white solid (9.4 g, sublimation point 85°/0.05 mm). The two solids were combined to yield 2,3,4,6-tetrafluoro[1,1'-biphenyl] (16.5 g, 48.6% yield, mp 86°-88°).

When the copper was omitted, (benzene)/(aniline) was 10, but the other conditions were substantially the same as above, the yield decreased to 36.8%.

EXAMPLE 3

Preparation of 4-Chloro[1,1'-biphenyl]

Under a dry nitrogen atmosphere a solution of 4-chloroaniline (38.3 g, 0.30 mole) in benzene (250 ml) was added dropwise during a one hour period to a stirred mixture of t-butyl nitrite (46.4 g, 0.45 mole) and copper powder (15.0 g, 0.24 mole) in benzene (2.5 l). After complete addition, the mixture was heated at 50° for 16 hours, then at reflux for 4 hours. The mixture was cooled to 20° and subjected to column chromatography on silica gel, elution with n-heptane. The solvent was evaporated under reduced pressure to leave a solid (52.2 g). The solid was dissolved in hot methanol (250 ml), treated with decolorizing charcoal, and the mixture filtered. The filtrate was cooled to produce an oil which solidified on standing. The solid was isolated by filtration to yield 4-chloro[1,1'-biphenyl] (35.3 g, mp 72.5°-75°). The mother liquor was evaporated under reduced pressure to leave a black solid (17.6 g). The black solid was purified by column chromatography on silica gel, n-heptane eluant, to produce 12.3 g of 4-chloro[1,1'-biphenyl] (mp 66°-70°). The two samples were combined to a total of 47.6 g, an 84% yield. The ir spectrum was consistent with the proposed structure.

The preparation of 4-chloro[1,1'-biphenyl] from the aforesaid reactants, but without copper, has been reported to give a 53% yield [*Chem. Abstr.*, 54, 4489h (1960)].

EXAMPLE 4

Preparation of 3-Chloro[1,1'-biphenyl]

In a manner similar to Example 1, the reaction of 3-chloroaniline (38.3 g, 0.30 mole) with t-butyl nitrite (46.4 g, 0.45 mole) in the presence of copper powder (15.0 g, 0.24 mole) and 4Å molecular sieves (powdered, 15.0 g) in benzene (1650 ml) produced 3-chloro[1,1'-biphenyl] (38.4 g, 67.6% yield, bp 96°/0.15 mm) as an oil. When the experiment was repeated the yield was 65.7%

The preparation of 3-chloro[1,1'-biphenyl] from the aforesaid reactants, but without copper, has been reported to give a 50% yield [*Chem. Abstr.*, 54, 4489h (1960)].

EXAMPLE 5

Preparation of 2-(3-Chloro-2-methylphenyl)thiophene

During a 30 minute period a solution of 3-chloro-2-methylaniline (8.3 g, 0.2 mole) in thiophene (100 ml) was added dropwise to a stirred mixture of t-butyl nitrite (30.9 g, 0.3 mole) and copper powder (10.0 g, 0.16 mole) in thiophene (1.9 l). After complete addition, the mixture was heated at 60° for two hours, then at reflux for approximately 18 hours. The reaction mixture was cooled, filtered, and the filtrate evaporated under reduced pressure to leave a residue. The residue was subjected to column chromatography on silica gel, elution with toluene. The toluene was evaporated under reduced pressure to leave a residue which was rechromatographed on silica gel, elution with n-heptane. The fractions which contained the desired product was combined and evaporated under reduced pressure to leave an oil. The oil was purified by distillation under reduced pressure to yield 2-(3-chloro-2-methylphenyl)-thiophene (25.9 g, 62.2% yield, bp 93°/0.1 mm). This experiment is designated Run 5/1 in the following tabulation of several experiments conducted with and without copper, but under otherwise similar conditions.

| Run | (Thiophene)/(Aniline) | Temp | Yield |
| --- | --- | --- | --- |
| 5/1 | 119 moles/mole | 84° | 62% |
| 5/2 | 55 | 70 | 54 |
| 5/3 | 56 | 74 | 50 |
| 5/4 | 55 | 70 | 71 |
| 5/5 | 55 | 70 | 37 |
| 5/6 | 10 | 40 | 48 |

| Run | (Thiophene)/(Aniline) | Temp | Yield |
|---|---|---|---|
| 5/7* | 10 | 70 | 34 |

*Run without copper; outside the scope of this invention.

On average, the yield was 54% with copper included, 34% without.

What is claimed is:

1. In a process for preparing a biaromatic compound of the formula

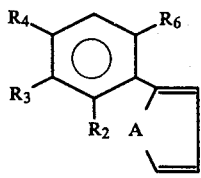

by treating an aniline derivative of the formula

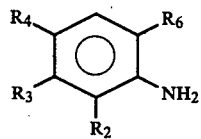

with a lower alkyl nitrite in a solvent of the formula

wherein $R_2$ is hydrogen, halogen, or lower alkyl, $R_3$ is hydrogen (unless $R_2$ is lower alkyl) or halogen, $R_4$ and $R_6$ are independently hydrogen or halogen, and A is —CH=CH—, —NH—, —CH=N—, O, or S, the improvement which comprises adding copper metal to the reaction mixture, thereby increasing the yield of the desired biaromatic compound.

2. The process of claim 1 wherein A is —CH=CH— or S.

3. The process of claim 2 wherein $R_2$ is methyl, $R_3$ is chlorine, and $R_4$ and $R_6$ are hydrogen.

4. The process of claim 3 wherein A is —CH=CH—.

5. The process of claim 3 wherein A is S.

6. The process of claim 2 wherein A is —CH=CH—.

7. The process of claim 6 wherein $R_3$ is chlorine and $R_2$, $R_4$ and $R_6$ are hydrogen.

8. The process of claim 6 wherein $R_4$ is chlorine and $R_2$, $R_3$ and $R_6$ are hydrogen.

9. The process of claim 6 wherein $R_2$, $R_3$, $R_4$ and $R_6$ are fluorine.

10. The process of claim 1 wherein the lower alkyl nitrite is selected from t-butyl nitrite and i-amyl nitrite.

* * * * *